(12) United States Patent  
Carr

(10) Patent No.: US 7,263,398 B2
(45) Date of Patent: Aug. 28, 2007

(54) APPARATUS FOR MEASURING INTRAVASCULAR BLOOD FLOW

(75) Inventor: Kenneth L. Carr, Woolwich, ME (US)

(73) Assignee: Meridian Medical Systems, LLC, Woolwich, ME (US)

( * ) Notice: Subject to any disclaimer, the term of this patent is extended or adjusted under 35 U.S.C. 154(b) by 811 days.

(21) Appl. No.: 10/603,851

(22) Filed: Jun. 25, 2003

(65) Prior Publication Data

US 2004/0267115 A1 Dec. 30, 2004

(51) Int. Cl.
*A61B 5/027* (2006.01)

(52) U.S. Cl. ........................................ 600/430; 600/505

(58) Field of Classification Search ............... 600/430, 600/504, 505; 607/100–101
See application file for complete search history.

(56) References Cited

U.S. PATENT DOCUMENTS

| | | |
|---|---|---|
| 4,557,272 A | 12/1985 | Carr |
| 4,583,556 A | 4/1986 | Hines et al. |
| 5,904,709 A | 5/1999 | Arndt et al. |
| 6,047,216 A | 4/2000 | Carl et al. |
| 6,210,367 B1 | 4/2001 | Carr |
| 6,408,204 B1 | 6/2002 | Hirschman |
| 6,475,159 B1 | 11/2002 | Casscells et al. |
| 6,496,736 B1 | 12/2002 | Carl et al. |
| 6,496,738 B2 | 12/2002 | Carr |

OTHER PUBLICATIONS

Diller, Wendy, "The Coming of Age of Vulnerable Plaque", Windhover Information, Inc. Start-up Nov. 2000, pp. 1-10.

*Primary Examiner*—Ruth S. Smith
(74) *Attorney, Agent, or Firm*—Cesari & McKenna, LLP

(57) ABSTRACT

Microwave apparatus for measuring the blood flow rate in a patient's blood vessel includes an intravascular catheter having proximal and distal ends and containing an inner coaxial cable forming a first antenna and an outer cable coaxial with the inner cable and forming a second antenna, the first antenna extending axially beyond the second antenna a selected distance. The apparatus also includes a control unit including a microwave transmitter, a microwave receiver and a processor controlling the transmitter and receiver. A diplexer is connected between the first and second antenna and the control unit to couple signals from the transmitter to the second antenna but not to the receiver and to couple signals from the first antenna to the receiver but not to the transmitter. The transmitter transmits microwave pulses to the first antenna which heat blood around that antenna. When the heated blood volume flows to the second antenna this is detected at the receiver which produces a detect signal. The processor measures the time interval between each pulse a subsequent detect signal and divides that time interval into the axial distance between the two antennas to compute the flow rate.

14 Claims, 1 Drawing Sheet

APPARATUS FOR MEASURING INTRAVASCULAR BLOOD FLOW

This invention relates to the measurement of intravascular blood flow. It relates especially to a method and apparatus for measuring such flow utilizing microwave radiometry.

BACKGROUND OF THE INVENTION

There are many instances when it is desirable or necessary to know the rate of flow of blood through a particular blood vessel of a patient for diagnostic purposes and in preparation for a surgical procedure. This flow rate may vary due to various factors such as the patient's blood pressure, presence of arthroscopic plaques which may partially occlude a blood vessel, etc.

The conventional method of measuring blood flow utilizes so-called thermodilution. An intravascular catheter carrying a temperature sensor such as a thermister or thermocouple is introduced into the pulmonary artery. Then saline is injected into the right atrium or ventricle to allow proper mixing of saline in the blood. Sometimes the saline is a room temperature but more often it is at a lower temperature, e.g. 4 C to increase the temperature difference from the patient's normal core temperature. The distance from the point of saline rejection to the sensor in the catheter is known more or less. Each time a saline bolus is injected, a clock is started to measure the time it takes for that bolus to flow to the sensor which thereupon emits a signal to stop the clock. The flow rate is determined by the dividing that fixed distance by the measured time interval.

In some situations, it may not be desirable to inject saline solution into the patient's blood stream. This is particularly so for neonatates whose blood volume is small. In addition, the distance between the point of saline injection and the sensor is not always known exactly. Those prior flow rate measuring devices which utilize temperature sensors such as thermisters and the like are also disadvantaged in that the sensors are not particularly sensitive and require recalibration because their thermal resistive characteristics may change over time.

SUMMARY OF THE INVENTION

Accordingly, it is an object of the present invention to provide an improved method of measuring intravascular blood flow.

Another object of the invention is to provide such a method which avoids the use of conventional temperature sensors such as thermisters, thermocouples and the like.

Another object of the invention is to provide a flow rate measuring method which does not require the introduction of a foreign fluid into the patient's blood stream.

Another object of the invention is to provide microwave apparatus for measuring a patient's intravascular blood flow in accordance with the above method and which produces all of the above advantages.

Other objects will, in part, be obvious and will, in part, appear hereinafter.

The invention accordingly comprises the several steps at the relation of one or more of such steps with respect to each of the others, and the apparatus embodying the features of construction, combination of elements and arrangement of parts which are adapted to effect such steps, all is exemplified in the following detailed description and the scope of the invention will be indicated in the claims.

Briefly, the present method utilizes microwave radiometry to measure intravascular blood flow. In accordance with the method, an intravascular catheter containing first and second axially spaced apart antennas is introduced into a patient's blood vessel. The catheter is connected to an extracorporial control unit which includes a microwave transmitter capable of delivering microwave energy pulses having a first frequency to the first antenna to heat a small volume of blood adjacent to that antenna. The control unit also includes a microwave receiver connected to the second antenna and which operates at a second frequency so that when the volume of blood heated by the first antenna passes the second antenna, that thermal anomaly is picked up by the second antenna which thereupon delivers a corresponding signal to the receiver. In addition, the control unit has a processor which controls the operation of the transmitter and receiver and can compute the time interval between each transmitter pulse and the corresponding signal picked up by the receiver and divide that time interval into the known distance between the two antennas to provide the flow rate of the blood in the patient's vessel, which rate may be displayed on a display device in the control unit.

Preferably, the first and second antennas in the catheter are coaxial with the second antenna, i.e. the receiving antenna, extending beyond the first or transmitting antenna. Preferably also, the catheter incorporates a diplexer for separating and bringing out from the catheter the two different frequency signals traveling between the catheter and the control unit.

When the subject catheter is inserted into a patient's blood vessel, the apparatus is able to quickly and accurately measure the blood flow rate in that vessel without the need to introduce foreign substances into that vessel.

BRIEF DESCRIPTION OF THE DRAWING

For a fuller understanding of the nature and objects of the invention, reference should be made to the following detailed description taken in connection with accompanying drawing, in which.

DESCRIPTION OF THE PREFERRED EMBODIMENT

Figure 1:
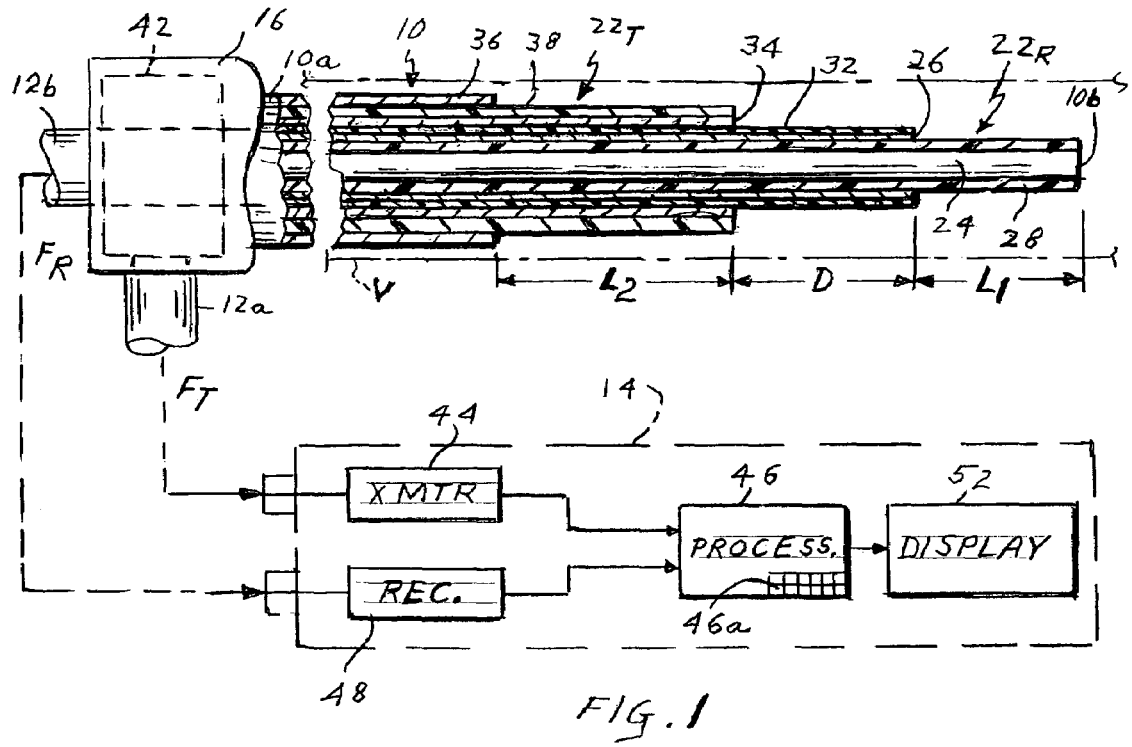
FIG. 1 is a diagrammatic view of apparatus for measuring intravascular blood flow in accordance with this invention.

Referring to FIG. 1 of the drawing, the present apparatus comprises a flexible catheter shown generally at 10 for insertion into a blood vessel V. Catheter 10 is connected by coaxial cables 12a and 12b to a control unit 14. The catheter has a proximal end 10a to which cables 12a and 12b are connected by way of a fitting or connector 16 and a distal end or tip 10b. In a typical procedure, the catheter may be inserted into the patient through a standard introducer inserted in the patient's neck. The introducer is typically 8.5 French, which the catheter may be 6 or 7 French. The catheter 10 goes from the jugular through the right side of the heart and then into the pulmonary artery.

As shown in FIG. 1, catheter 10 incorporates coaxial inner and outer antennas $22_R$ and $22_T$. The inner antenna $22_R$ comprises a coaxial cable consisting of an inner conductor 24 and an outer conductor 26 separated by a dielectric layer 28, the outer conductor 26 being surrounded by a thin dielectric sleeve 32. The inner conductor 24 may be formed as a tube to accept a conventional guide wire (not shown) to help guide the catheter 10 into vessel V. The outer antenna $22_T$ consists of an inner conductor 34 and an outer conductor 36 separated by a dielectric layer 38. As seen in FIG. 1, the innermost conductor 24 projects beyond the next outer conductor 26 a distance $L_1$ and constitutes antenna $22_R$. Also, the outermost conductor 36 is set back from the next inner conductor 34 a distance $L_2$ thus forming the outer antenna $22_T$. The two antennas $22_R$ and $22_T$ are spaced apart axially a distance D, the conductors in that distance D basically constituting a short transmission line. Preferably, the inner coaxial cable constituting antenna $22_R$ is slidable relative to conductor 34 and remaining outer conductors and fitting 16, enabling the adjustment of the distance D between the two antennas $22_R$ and $22_T$.

At fitting 16, the proximal ends of conductors 24, 26, 34 and 36 are connected by way of a passive diplexer 42 (FIG. 2) in fitting 16 to the coaxial cables 12a and 12b. Preferably, the implantable segment of catheter 10 has a protective dielectric outer coating, e.g. of PTFE, (not shown).

Still referring to FIG. 1, the control unit 14 comprises a microwave transmitter 44 which operates under the control of a processor 46 in unit 44 to deliver microwave pulses at a fixed frequency $F_T$ via cable 12a to antenna $22_T$ in catheter 10. Preferably, transmitter 24 is a solid state programmable transmitter which may operate at, say, 915 MHz and may have a maximum power output of 0 to 120 watts. Such a transmitter is available from Meridian Medical System, Inc. Acton, Mass. That transmitted power causes antenna $22_T$ to emit electromagnetic radiation which heats the blood in the region $L_2$ surrounding that antenna.

The control unit 14 also includes a microwave receiver 46 which receives signals $F_R$ from antenna $22_R$ via cable 12b. Preferably, the radiometer is a Dicke-switch radiometer of the type available from Meridian Medical System, Inc., Ayer, Mass. It has a radiometer frequency in the range of 3.7 to 4.2 GHz, with a center frequency of 4.0 GHz. When a temperature anomaly is picked up from the region $L_1$ surrounding antenna $22_R$, that signal $F_R$ is detected by receiver 48 which delivers a corresponding output signal to processor 46. The processor thereupon computes the blood flow rate and sends a control signal to a display device 52, e.g. CRT, printer, plotter, etc., in unit 14 which displays that flow rate.

The pulse rate of the transmitter 44 and the information displayed on display 52 may be controlled by entering appropriate data into the processor via the processor's keyboard 46a.

Also as noted above, the distance D between the two antennas $22_R$ and $22_T$ may be varied to optimize the performance of the two antennas, that distance also being entered into the processor 46 via keyboard 46a.

Figure 2:
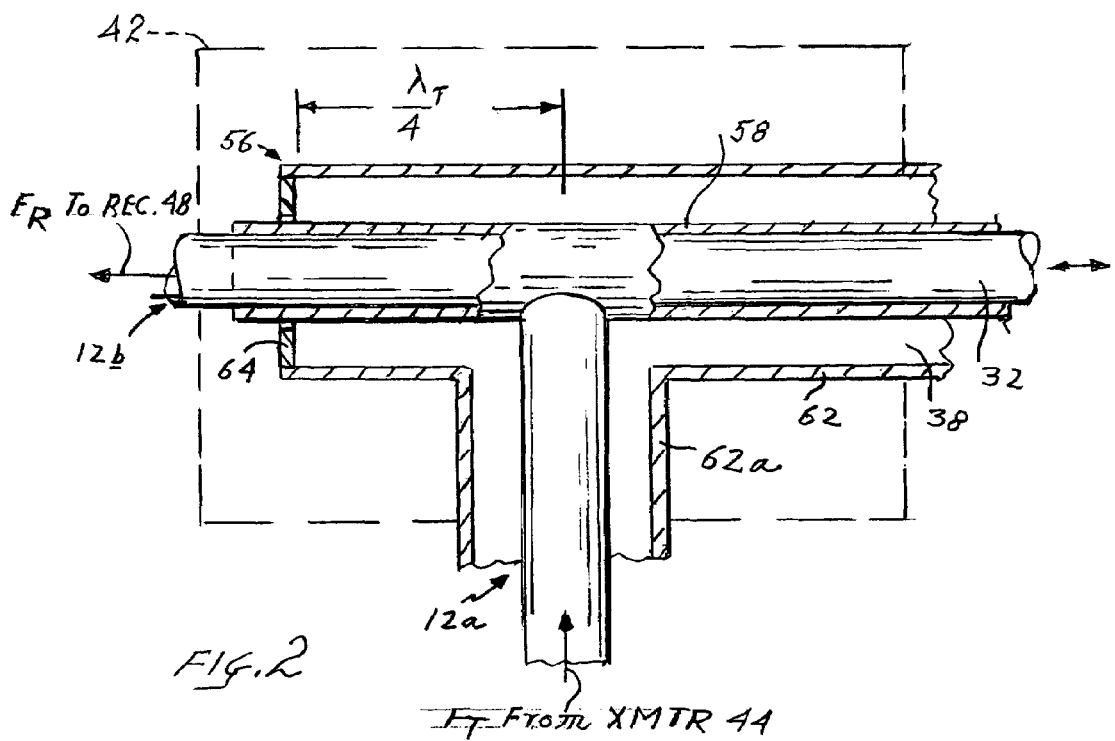
FIG. 2 is a sectional view of the diplexer component of the FIG. 1 apparatus.

Refer now to FIG. 2 which shows the diplexer 42 in detail. As seen there, the diplexer includes a quarter-wave ($_T$/4) stub to bring out the signal $F_R$ from the inner antenna $22_R$. The stub also provides a matched 90 bend to separate and bring out the signal $F_T$ from the outer antenna $22_T$ so that the signal from the transmitter 44 is not coupled to the receiver 46 and vice versa.

While it is known in the art to use a quarter-wave stub to support the center conductor of an antenna, the present diplexer has a tubular inner conductor 58 which receives the coaxial table 24-32 comprising the inner antenna $22_R$ that provides the signal $F_R$. That conductor 58 may be an extension of the antenna conductor 34. Surrounding and being insulated from conductor 58 is a coaxial outer conductor 62 which may be an extension of antenna conductor 36. The two diplexer conductors 58 and 62 are shorted by an end plate 64. Conductor 58 has a branch 58a which is brought out through a tubular branch 62a of conductor 62 to enable the delivery of the signal $F_T$ to antenna $22_T$. Preferably, the coaxial cable 24-32 is slidable to some extent along conductor 58 to vary the antenna distance D as described above.

The illustrated diplexer 42 provides distinct advantages in that it separates the concentric cables from antennas $22_R$ and $22_T$ in FIG. 1 into two separate cables and it allows those cables to be mechanically positioned independently.

When catheter 10 is inserted into a patient's blood vessel V and the control unit 14 is activated, transmitter 44 applies microwave pulses to antenna $22_T$. The microwave energy heats the blood in the volume $L_2$ around that antenna. That volume then travels to the region $L_1$ around antenna $22_R$ which senses the increased thermal energy from that volume and applies a corresponding signal to receiver 48. The processor 46 thereupon computes the elapsed time between the transmitted signal and the received signal and divides that time into the distance D between the two antennas to produce the measured blood flow rate which may then be displayed by the display device 52. All of this is done quickly and accurately without the necessity of introducing any foreign substance into the patient's blood stream. Moreover, there are no components in the catheter whose ages may effect their ability to accurately heat and detect the rate of flow of the blood in the vessel V.

As noted above, the spacing D of the two antennas $22_R$ and $22_T$ may be adjusted to optimize the performance of the antennas and of the catheter 10 as a whole. As described above, the diplexer 42 accommodates such sliding movement while still separating the signals on the two antennas so that the signal transmitted by antenna $22_T$ is not received by the receiver 48 and conversely, the signal received by antenna $22_R$ is not coupled to the transmitter 44.

It will thus be seen that the objects set forth above, among those made apparent from the preceding description, are efficiently attained. Also, certain changes may be made in carrying out the above method and the construction set forth without departing from the scope of the invention. For example, the positions of the two antennas $22_R$ and $22_T$ may be reversed in which case the diplexer would have a length $(_R/4)$. Therefore, it is intended that all matter contained in the above description or shown in the accompanying drawing shall be interpreted as illustrative and not in a limiting sense.

It is also to be understood that the following claims are intended to cover all of the generic and specific features of the invention described herein.

What is claimed is:

1. Microwave apparatus for measuring blood flow rate in a patient's blood vessel, said apparatus comprising, an intravascular catheter having proximal and distal ends and containing an inner coaxial cable forming a first antenna and an outer cable coaxial with the inner cable and forming a second antenna, said first antenna extending axially beyond the second antenna a selected distance;

an extracorporeal control unit including a microwave transmitter which transmits signals to the catheter, a microwave receiver which receives signals from the catheter, and a processor controlling the transmitter and receiver, said processor including means responsive to the timing of the transmitted and received signals for measuring said blood flow rate, and a diplexer connected between said first and second antennas and the control unit for coupling signals from the transmitter to one of the antennas but not to the receiver and for coupling signals from the other of the antennas to the receiver but not to the transmitter.

2. The apparatus defined in claim 1 wherein
the transmitter transmits signals of a first frequency, and the receiver is designed to receive signals of a second frequency different from the first frequency.

3. The apparatus defined in claim 1 wherein the diplexer is contained in a proximal end of the catheter.

4. The apparatus defined in claim 1 wherein
the transmitter transmits signal pulses to said one of the antennas and, each time, sends a transmit signal to the processor;
the receiver sends a detect signal to the processor each time it detects a signal from said other of the antennas, and
said processor includes means for determining the elapsed time between the reception of a transmit signal and a subsequent detect signal and means for dividing that time into the axial distance between said first and second antennas to compute said flow rate.

5. The apparatus defined in claim 4 wherein the control unit also includes a display device controlled by the processor for displaying the flow rate.

6. The apparatus defined in claim 1 wherein the inner coaxial cable is slidable relative to the outer coaxial cable so as to allow adjustment of said selected distance.

7. The apparatus defined in claim 1 wherein the diplexer is mounted to a proximal end of the catheter and includes
radially spaced-apart inner and outer tubular conductors surrounding a segment of said inner coaxial cable and connected electrically to said outer coaxial cable;
a tubular side branch extending from said outer conductor;
a branch conductor extending from said inner conductor through said side branch to form a port;
a short circuit between said inner and outer conductors at a distance from said branch conductor to form a quarter wavelength stub at the frequency of the signal carried by the outer antenna.

8. The apparatus defined in claim 7 wherein the inner coaxial cable is slidable relative to the outer coaxial cable and inner conductor so as to allow adjustment of said selected distance.

9. Microwave apparatus for measuring the blood flow in a patient's blood vessel, said apparatus comprising
an intravascular catheter having proximal and distal ends and containing an inner coaxial cable forming a first antenna and an outer coaxial cable forming a second antenna, said first antenna extending axially beyond the second antenna a selected distance;
a diplexer at the proximal end of the catheter, said diplexer having radially spaced-apart inner and outer conductors, said inner conductor snugly receiving the inner coaxial cable and the inner and outer conductors being connected electrically to the outer coaxial cable, said outer conductor having a tubular branch oriented substantially 90° relative to the inner conductor and said inner conductor having a connection extending through said branch and being spaced from corresponding shorted ends of the inner and outer conductors to form a quaffer wave stub at the frequency of the signal carried by the second antenna, and
a control unit including a microwave transmitter which transmits signals via the diplexer to the catheter, a microwave receiver which receives signals via the diplexer from the catheter and a processor controlling the transmitter and receiver, said processor including means responsive to the timing of the transmitted and received signals for measuring said blood flow rate.

10. The apparatus defined in claim 9 wherein the inner coaxial cable is slidable lengthwise relative to the outer coaxial cable and an inner conductor so as to allow adjustment of said selected distance.

11. The apparatus defined in claim 9 wherein the inner coaxial cable has an open-ended tubular inner conductor which extends the length of the catheter.

12. Microwave apparatus for measuring blood flow in a patient's blood vessel, said apparatus comprising
an intravascular catheter having proximal and distal ends;
a diplexer at the proximal end of the catheter, said diplexer including
a radially outer tubular conductor having a tubular side branch, and
a radially inner tubular conductor spaced from the outer conductor and having a connection extending through the side branch of the outer conductor to the out-side to form a first port, said inner and outer conductors having proximal ends which are short circuited to form a quarter wave stub between said proximal ends and the side connection of the inner conductor;
a first antenna at the distal end of the catheter, said first antenna including radially inner and outer electrically insulated tubular conductors connected electrically to the respective inner and outer conductors of the diplexer;
a second antenna at the distal end of the catheter spaced axially beyond the first antenna, said second antenna including a coaxial cable having an inner conductor and which extends through the inner conductor of the diplexer to the outside to form a second port, and
a control unit including a microwave transmitter which transmits signals via the diplexer to the catheter, a microwave receiver which receives signals via the diplexer from the catheter and a processor controlling the transmitter and receiver, said processor including means responsive to the timing of the transmitted and received signals for measuring said blood flow rate.

13. The apparatus defined in claim 12 wherein the coaxial cable is slidable within the inner conductors of the first antenna and diplexer to adjust the axial distance between the first and second antennas.

14. The apparatus defined in claim 12 wherein the inner conductor of the coaxial cable of the second antenna is an open-ended tube adapted to slidably receive a guide wire.

* * * * *